United States Patent
Kuo et al.

(10) Patent No.: US 9,545,064 B2
(45) Date of Patent: Jan. 17, 2017

(54) TISSUE CULTURING METHOD, CULTURING METHOD OF FERNS AND EXPLANT OBTAINED THEREFROM

(71) Applicant: Chunghwa Picture Tubes, Ltd., Taoyuan (TW)

(72) Inventors: Chou-Chiang Kuo, New Taipei (TW); Chin-Wen Ho, Taipei (TW); Kai-Ping Wang, Taipei (TW); Yu-Syuan Wu, Taipei (TW); Yung-Ting Tsai, Taipei (TW)

(73) Assignee: Chunghwa Picture Tubes, Ltd., Taoyuan (TW)

( * ) Notice: Subject to any disclaimer, the term of this patent is extended or adjusted under 35 U.S.C. 154(b) by 326 days.

(21) Appl. No.: 14/161,687

(22) Filed: Jan. 23, 2014

(65) Prior Publication Data
US 2015/0132852 A1 May 14, 2015

(30) Foreign Application Priority Data
Nov. 8, 2013 (TW) .............................. 102140712 A

(51) Int. Cl.
*A01H 4/00* (2006.01)
*A01H 9/00* (2006.01)

(52) U.S. Cl.
CPC ................. *A01H 4/008* (2013.01); *A01H 9/00* (2013.01)

(58) Field of Classification Search
None
See application file for complete search history.

(56) References Cited

U.S. PATENT DOCUMENTS 6,218,184 B1  4/2001  Hasegawa

FOREIGN PATENT DOCUMENTS

| CN | 102845309 A | 1/2013 |
|----|-------------|--------|
| TW | 200948272   | 12/2009 |
| TW | I323641     | 4/2010 |

OTHER PUBLICATIONS

Fernandez et al. Influence of tissue culture conditions on apogamy in *Dryopteris affinis* sp. affinis. Plant Cell, Tissue and Organ Culture 45: 93-97, 1996.*
Garcia et al. Sporophyte regeneration of *Platycerium bifurcatum* (Cav.) C.Chr. from in vitro germinated spores. Biotecnologia Vegetal vol. 13, No. 2: 99-105, Junio 2013.*
English translation of Garcia et al. pp. 1-21.*
Marimuthu et al. Ex situ conservation of two threatened ferns of the Western Ghats through in vitro spore culture. Journal of Threatened Taxa Jul. 2011, 3(7): 1919-1928.*
Menendez et al. Exogenous and endogenous growth regulators on apogamy in *Dryopteris affinis* (Lowe) *Fraser-Jenkins* sp. affinis. Plant Cell Rep. (2006) 25: 85-91.*
Zheng et al. Plant regeneration of the arsenic hyperaccumulator *Pteris vittata* L. from spores and identification of its tolerance and accumulation of arsenic and copper. Acta Physiol. Plant Polish Academy of Science 2007, 7 pp.*
Jiang Shengjun et al., "Progress in Tissue Cultures in Vitro of Ferns", 2002, pp. 651-656, vol. 29, supplement, Acta Horticulturae Sinica.
Cheema, et al., "In vitro induction and differentiation of gametophytic callus in Ceratopteris thalictoroides", 1992, pp. 74-77, 8(1-2), Indian Fern Journal.
Yung-Ting Tsai, etd-0915109-125141, In vitro culture and somatic embryogenesis of Davallia mariesii Moore ex Bak, Jul. 28, 2009.
A. Kuriyama et. al., Production of sporophytic structures from gametophytes by cytokinin in Equisetum arvense, Naturwissenschaften 77, 31-32(1990).
Tissue culture propagation techniques of native cut leaves plants, Tainan District Agricultural special hearing 40: 1/4 pages (Jun. 2002), C-J Chen, S-Y Hsieh.
In vitro culture and somatic embryogenesis of Davallia mariesii Moore ex Bak, Yung-Ting Tsai, Thesis for Master of Science Department of Bioengineering, Tatung University, Jul. 2009, paragraph 3.1.2 of p. 17, paragraph 3.1.6 of p. 21, table 1 and table 2.

* cited by examiner

*Primary Examiner* — June Hwu
(74) *Attorney, Agent, or Firm* — Winston Hsu; Scott Margo

(57) ABSTRACT

A tissue culturing method includes following steps: providing a chopped gametophyte, generating calluses by culturing the chopped gametophyte, and performing apogamic regeneration of sporophytes, by culturing the calluses in a culture fluid to develop the sporophytes from the calluses. The present invention also provides a tissue culturing method of ferns and an explant.

7 Claims, 5 Drawing Sheets

TISSUE CULTURING METHOD, CULTURING METHOD OF FERNS AND EXPLANT OBTAINED THEREFROM

BACKGROUND OF THE INVENTION

1. Field of the Invention

The present invention relates to a culturing method, and more particularly, to a tissue culturing method of vascular plants and an explant obtained therefrom.

2. Description of the Prior Art

Vascular plants, also known as tracheophytes, are defined as a large group of land plants having lignified tissues for conducting water and minerals throughout the entire plants; vascular plants comprise ferns. Ferns are characterized by reproduction of spores and alternation of generations. Although such vascular plants can spread their spores through various intermedia (such as wind and water) to propagate themselves, the spores are difficult to germinate due to poor competitiveness and environmental resistance in comparison with other fungi and bacteria. These vascular plants are less likely to be used in industries, even for highly valuable species such as ferns in the Davalliaceae and Drynariaceae families which have pharmaceutical properties, since they have poor reproduction systems.

In the conventional arts, tissue culture systems such as spore sterile propagation are used for mass propagation of said vascular plants. In the spore sterile propagation, a sterilized process is first carried out on spores of said vascular plants, followed by culturing the spores in artificial media for germinating. Under such culturing system, however, the spores require a long culturing period to germinate, and also may form disabled sporophytes due to the limitation of the artificial media, which results in poor propagation. This means that said vascular plants cannot be mass reproduced under the conventional tissue culture system.

There is therefore an urgent need for developing a new strategy to culture said vascular plants that is both effective and efficient.

SUMMARY OF THE INVENTION

It is one of the objectives of the present invention to provide a culturing method of ferns which facilitates the reproduction of ferns accomplished via an apogamy, leading to effective sporophyte regeneration.

It is another one of the objectives of the present invention to provide a tissue culturing method which facilitates the reproduction of vascular plants accomplished via an apogamy, so that dramatic reproduction of the vascular plants can be achieved.

It is another one of the objectives of the present invention to provide a tissue culturing method which induces the vascular plants to directly regenerate sporophytes through somatic embryogenesis, thereby simplifying the tissue culturing process and obtaining fully developed sporophytes.

It is another one of the objectives of the present invention to provide an explant, which is capable of being reproduced via an apogamous process, and can be used for mass production of the vascular plants.

To achieve said objectives, the present invention provides a tissue culturing method comprising following steps: providing a chopped gametophyte; generating a callus, by culturing the chopped gametophyte till the chopped gametophyte generates the callus; and performing apogamic regeneration of a sporophyte, by culturing the calluses in a culture fluid to develop the sporophyte from the callus.

To fulfill said objectives, the present invention also provides a culturing method of ferns comprising: providing a chopped gametophyte of ferns; generating a callus, by culturing the chopped gametophyte of ferns till the chopped gametophyte generates the callus; and performing apogamic regeneration of a sporophyte, by culturing the calluses in a culture fluid to develop the sporophyte from the callus.

In one preferred embodiment, the step of generating the callus further comprises inducing the chopped gametophyte to generate the callus and proliferating a generated callus.

In one preferred embodiment, the step of apogamic regeneration of the sporophyte further comprises sporophyte induction, by inducing the callus to form the sporophyte, and sporophyte proliferation, by proliferating a formed sporophyte.

In one preferred embodiment, the culture fluid comprises 1 wt % to 5 wt % carbon source.

In one preferred embodiment, the culture fluid comprises ½ MS medium and 20 g/L sucrose.

In one preferred embodiment, the step of apogamic regeneration of the sporophyte comprises culturing the callus in a first culture fluid to induce the generating of the sporophyte from the callus, and then culturing a generated sporophyte in a second culture fluid to induce the proliferation of the generated sporophyte, wherein the first culture fluid and the second culture fluid comprise different compositions.

In one preferred embodiment, the first culture fluid comprises cytokinins being selected from a group of N6-(delta 2-isopentenyl)-adenine (2ip), 6-benzylaminopurine (BA) and kinetin.

In one preferred embodiment, the tissue culturing method further comprises acclimatization of the sporophyte, by isolating the sporophyte from the culture fluid and transplanting the sporophyte.

In one preferred embodiment, the step of apogamic regenerating of sporophyte comprises shaking culture of the callus.

In one preferred embodiment, the tissue culturing method further comprises transplanting the sporophyte in a solid medium till a plant is grown.

To fulfill the above objectives, the present invention further provides an explant, comprising a plurality of calluses massed in a round having a diameter between 0.19 cm and 0.25 cm.

In one preferred embodiment, the explant is obtained through a process comprising following steps: providing a chopped gametophyte; culturing the chopped gametophyte till the chopped gametophyte generates a callus; and proliferating the callus till a plurality of the calluses is generated and massed in the round to obtain the explant.

DETAILED DESCRIPTION

The present invention provides a mass production strategy for vascular plants, such as ferns, which induces the vascular plants to regenerate sporophytes through somatic embryogenesis, thereby achieving fast and effective development under a short culturing period. Since the sporophyte regeneration of the vascular plants in the present invention is accomplished through somatic embryogenesis rather than organogenesis, the culturing of the vascular plants can be achieved in a time-efficient procedure with some processes, such as spores germination and rooting, being omitted. With such performance, the present invention can significantly shorten the culturing period of the vascular plants and increase the germination rate of the vascular plants, thus enabling mass production.

In the present invention, a tissue culturing method is provided, by using a gametophyte of vascular plants as an explant, chopping up the gametophyte and culturing a chopped gametophyte in a medium to induce the chopped gametophyte to generate embryogenic calluses, and finally form the calluses in a callus round. Then, said embryogenic callus is further induced to regenerate a sporophyte directly through an apogamous process. In this way, the germination of spores, as well as the survival of acclimatized plants after acclimatization, can all be dramatically improved in the present invention. Also, it is demonstrated that the regenerated sporophyte obtained in the present invention is diploidic.

Figure 1:
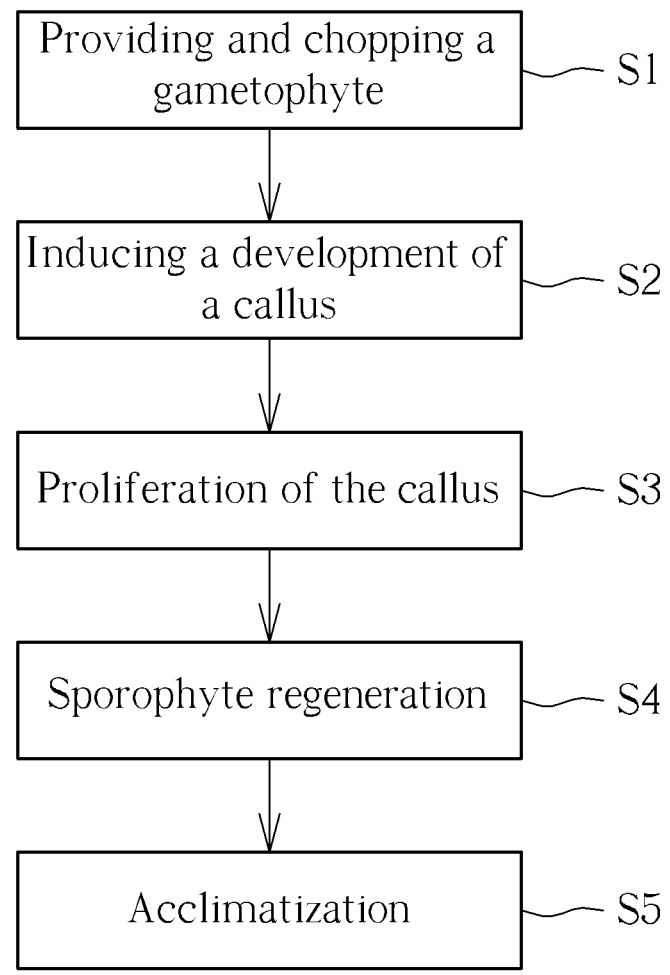
FIG. 1 to FIG. 4 are diagrams illustrating a procedure of a tissue culturing method according to an embodiment of the present patent application.

FIG. 1 to FIG. 4 illustrate schematic procedures of a tissue culturing method in accordance with a preferred embodiment of the present invention. As shown in FIG. 1, the tissue culturing method of the present embodiment primarily comprises providing a gametophyte of vascular plants and breaking tissues thereof (step S1). The vascular plants of the present embodiment refer to plants having notable gametophyte generation (being haploid), such as ferns, and is preferably for ferns having pharmaceutical properties, such as ferns of the Davalliaceae family. The gametophyte of the present embodiment can be obtained through spore sterile propagation or other culturing methods, wherein the culturing method is not limited to what is detailed herein. In the present invention, the breaking of tissue can be achieved by any possible means to generate wounds, including cutting, chopping, smashing and tearing but is not limited thereto.

Figure 2:
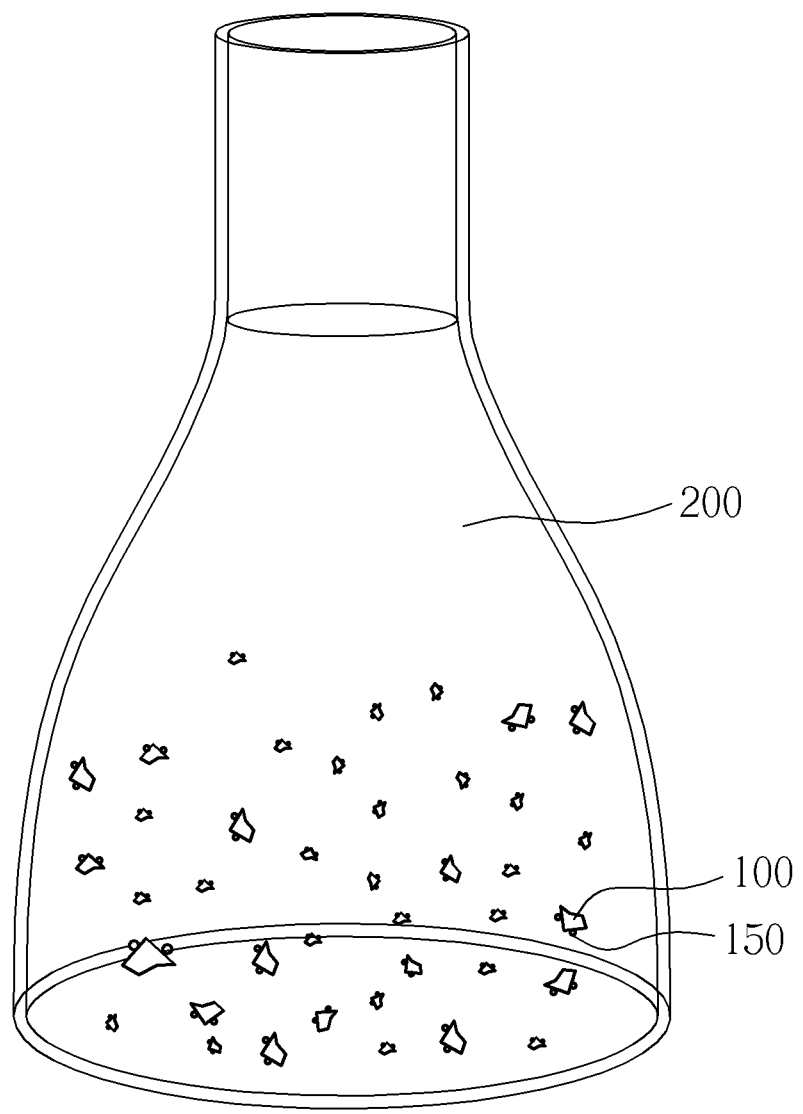

Referring to FIG. 1 and FIG. 2, the tissue culturing method of the present embodiment also comprises inducing a development of a callus 150, by culturing a chopped gametophyte 100 in a medium 200 till the chopped gametophyte 100 generates the callus 150 (step S2). In the present embodiment, the culturing of the chopped gametophyte 100 is preferably carried out by continually and evenly attaching the chopped gametophyte 100 in the medium 200, probably through a suspending culture and a shaking culture but not limited thereto. In addition, the chopped gametophyte 100 requests enough basic salts (including nitrogenous salts, phosphorous salts, potassium salts, and calcium salts) and nutrients during the culturing process. Further, the chopped gametophyte 100 is preferably sub-cultured periodically: for example, every twenty to forty days (more preferably, every thirty days), so as to effectively generate the callus 150. The medium 200 comprises basic salts (including nitrogenous salts, phosphorous salts, potassium salts, and calcium salts) and can also comprise a small amount (such as 1 wt % to 5 wt %) of carbon source to facilitate the generating of the callus 150. The medium 200 can further comprise a growth regulator of plant, such as 1-Naphthaleneacetic acid (NAA), 6-Furfurylamino-purine (kinetin) or cytokinins (including N6-(delta 2-isopentenyl)-adenine (2ip) and 6-benzylaminopurine (BA)) to further facilitate the generating of the callus 150.

Figure 3:
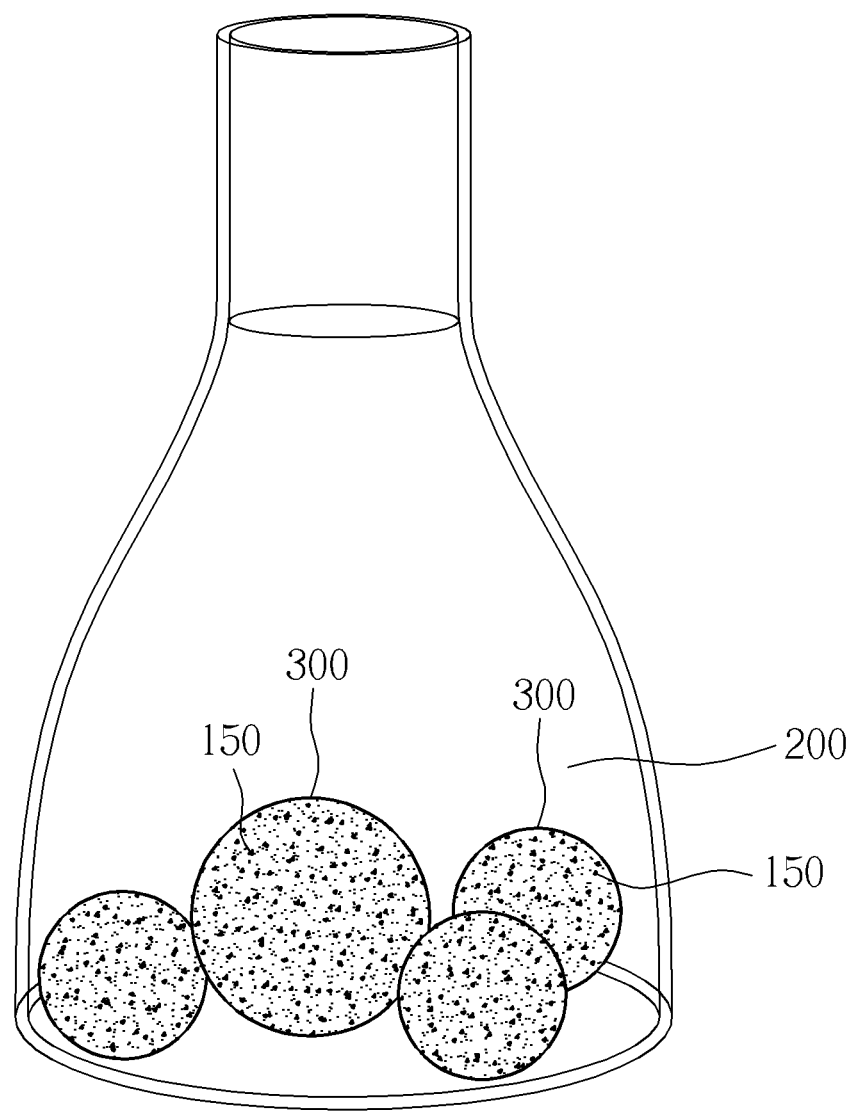

The tissue culturing method of the present embodiment comprises proliferation of the generated callus 150, by isolating the generated callus 150 from the chopped gametophyte 100 and culturing the generated callus 150 in the medium 200 (step S3). It is noted that the generated callus 150 requests a higher amount of basic salts and nutrients in this stage but shares the same culturing conditions as that of step S2. Similarly, in order to facilitate the proliferating of the callus 150, the callus 150 is preferably sub-cultured every ten to forty days and more preferably for every fifteen days. The callus 150 can be fast proliferated and massed in a round, after which a callus round 300 is formed as illustrated in FIG. 3. In a preferable embodiment, the callus round 300 has a diameter of 0.19 cm to 0.25 cm, preferably 0.24 cm. The callus round 300 can be used as an explant to regenerate sporophyte and which can be further put in use for mass produce the vascular plants.

Figure 4:
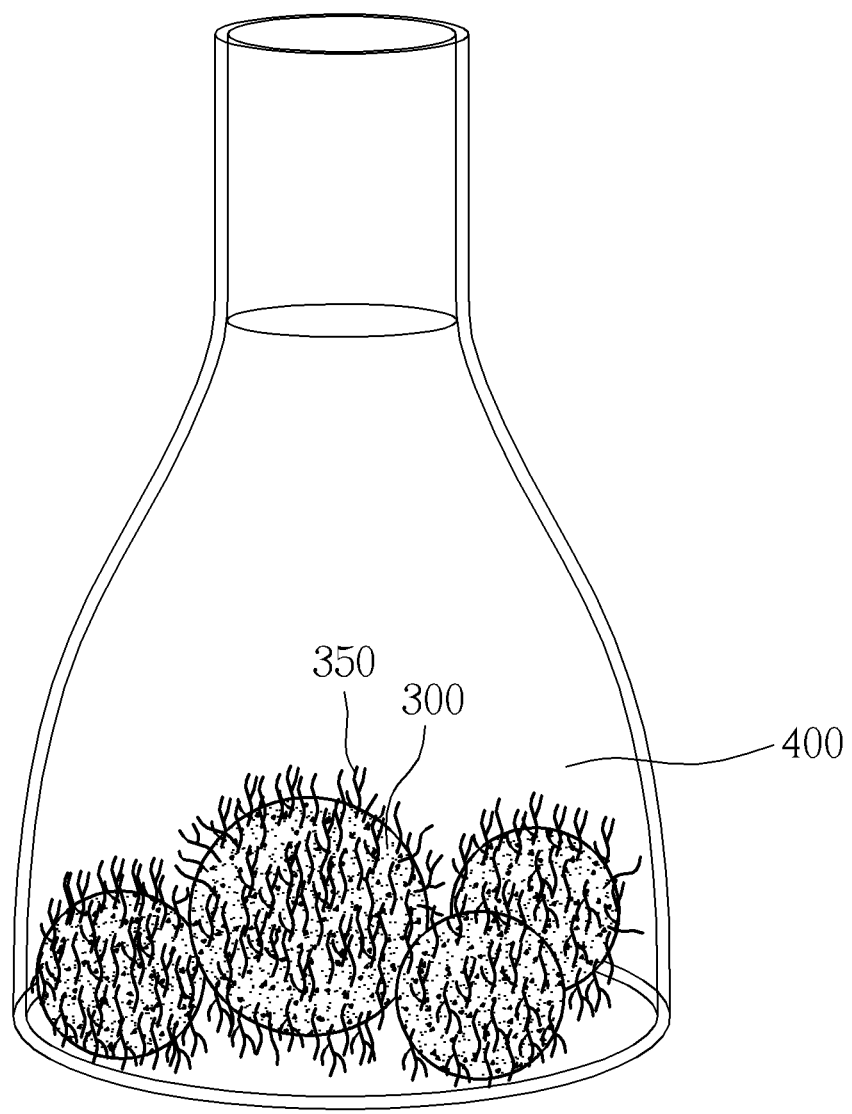

Referring to FIG. 1 and FIG. 4, the tissue culturing method of the present embodiment comprises regenerating sporophyte 350, by culturing the callus round 300 in a culture fluid 400 to develop the sporophyte 350 from the callus round 300 (step S4). In the present embodiment, the culturing of the callus round 300 is preferably carried out by continually and evenly attaching the callus round 300 to the culture fluid 400, for example culturing of the callus round 300 through shaking culture, but this is not limited thereto. The callus round 300 requests enough basic salts (including nitrogenous salts, phosphorous salts, potassium salts, and calcium salts), less carbon source (for example 1 wt % to 5 wt %), and nutrients during the culturing, and is preferably sub-cultured every ten to twenty days and more preferably for every fifteen days, so as to regenerate sporophyte 350 effectively. In the present embodiment, the culture fluid 400 preferably comprises cytokinins, such as N6-(delta 2-isopentenyl)-adenine (2ip) and 6-benzylaminopurine (BA), to further facilitate the callus round 300 to develop the sporophyte 350.

The tissue culturing method of the present embodiment can also comprise acclimatizing the sporophyte 350, by isolating the sporophyte 350 from the callus round 300 and transplanting the sporophyte 350 in a solid medium (not shown in the figures) till they grow into a plant (step S5). The solid medium comprises any possible culturing materials which are capable of being used for culturing vascular plants. Said culturing materials are diverse in accordance with various kinds of plants. In the present embodiment, the solid medium preferably comprises sterile mixed materials including sphagna, vermicnlite, charcoal rotten leaves and broken brick.

Through the present invention, the tissue culturing method mainly induces the chopped gametophyte to generate and proliferate embryogenic calluses, and further induces said embryogenic calluses to regenerate sporophytes via an apogamous process. The tissue culturing method only uses chopped gametophytes and a culture fluid to induce the vascular plants to directly regenerate sporophytes through somatic embryogenesis, and complicated and time-consuming processes, such as spore germination, can be omitted. The present invention can therefore achieve reproduction of the vascular plants via an easy and convenient procedure. Also, due to the advantages of the present invention, the tissue culturing method can be further put to use on many vascular plants around the world, such as ferns.

Figure 5:
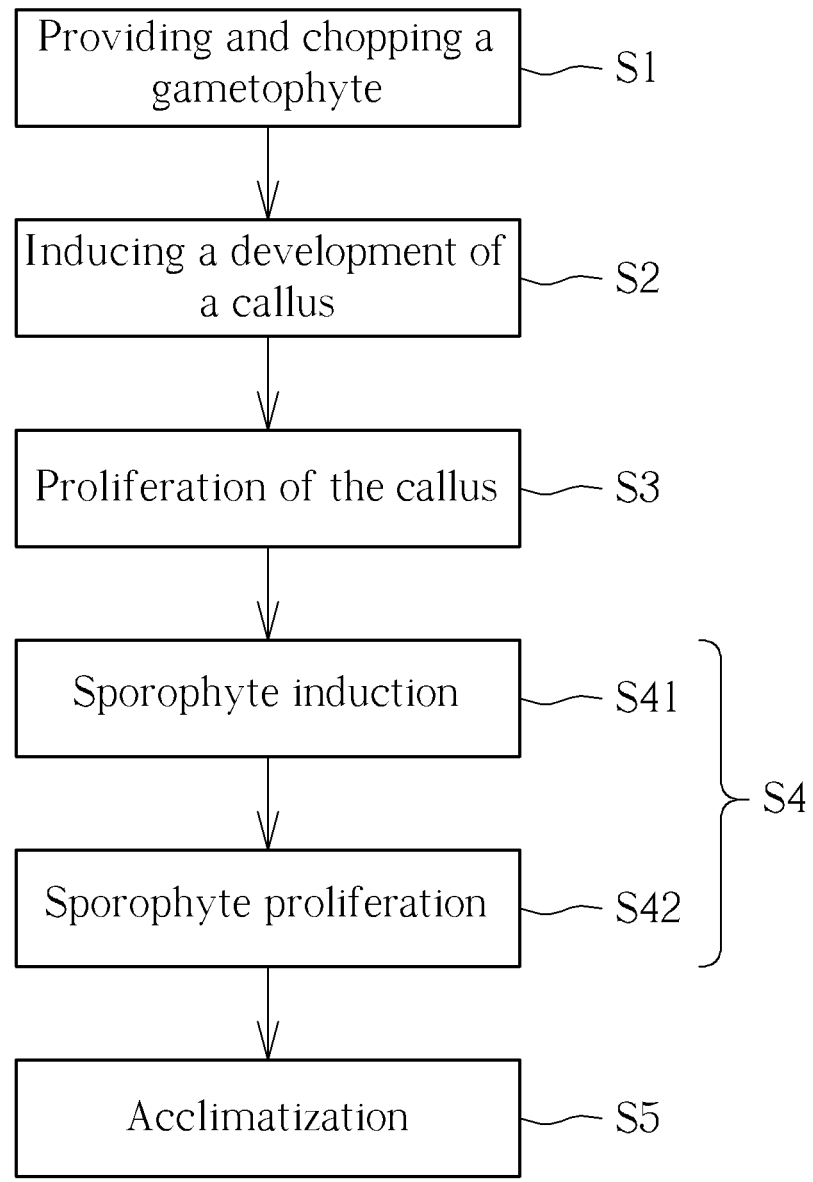
FIG. 5 is a diagram illustrating a procedure of a tissue culturing method according to another embodiment of the present patent application.

FIG. 5 illustrates a schematic procedure of a tissue culturing method in accordance with another preferred embodiment of the present invention. It is noted that differences between the aforementioned embodiment and the present embodiment are characterized by sporophyte induction (step S41) and sporophyte proliferation (step S42) in step S4 of the present embodiment. The sporophyte induction comprises culturing the callus round 300 in a first culture fluid to induce the callus round 300 to regenerate the sporophyte 350. In step S41, the culturing of the callus round 300 is preferably carried out through a shaking culture which undergoes a subculture every ten to twenty days, and more particularly, for fifteen days.

The first culture fluid comprises basic salts (including nitrogenous salts, phosphorous salts, potassium salts, and calcium salts), a small amount of carbon source, (such as 1 wt % to 5 wt %, preferably for 2 wt %), and cytokinins, such as N6-(delta 2-isopentenyl)-adenine (2ip) and 6-benzylaminopurine (BA), to facilitate the callus round 300 to regenerate the sporophyte 350. In the following, the sporophyte proliferation (step S42) comprises isolating a regenerated sporophyte 350 from the callus round 300 and culturing the regenerated sporophyte 350 in a second culture fluid. The second culture fluid comprises basic salts (including nitrogenous salts, phosphorous salts, potassium salts, and calcium salts) and a small amount of carbon source but does not have any growth regulator or cytokinins. Under such an arrangement, the sporophyte 350 can quickly develop and proliferate at high efficiency.

In the present embodiment, the induction and proliferation of the sporophyte 350 are carried out in two separate steps. Since the sporophyte 350 request various nutrients in different stages, it is more efficient to increase the entire culturing efficiency of the sporophyte 350 while inducing and proliferating the sporophyte 350 in separate steps.

A practical example of the tissue culturing method of the present invention is provided, by culturing a fern of the Davalliacea family, such as *Davallia mariesii*. In the present example, a leaf of the fern and immature spores thereon are collected and cultured together in a sterile culturing medium, which is sub-cultured monthly till a prothallium is obtained. The prothallium can also be obtained through other methods and is not limited to what has been previously described.

Example 1

The prothallium is chopped up into small pieces being 0.1 cm to 0.2 cm in width and cultured (suspending culture) in a medium, wherein the medium comprises ½ MS medium (Murashige and Skoog, 1962) having a composition as shown in TABLE 1. In other examples, the medium can also comprise Knop medium (Murashige and Skoog, 1962) or knudson medium (Knudson, 1946). Precisely, 0.1 g chopped prothallium are cultured in 10 ml ½ MS medium, which are shake cultured at 85 rpm for forty to eighty days, and preferably at 23° C. to 25° C. and 11 to 14 $\mu mol^{-2}\ s^{-1}$ (Light:Dark=16:8) for sixty days, and are sub-cultured every thirty days.

In another example of the present invention, the medium comprises ½ MS medium and at least one of 0 to 5 mg/l Naphthaleneacetic acid (NAA) and 0 to 5 mg/l 6-Furfurylamino-purine (kinetin). In a preferred embodiment, the medium comprises ½ MS medium, 1 mg/l NAA and 1 mg/l kinetin, so as to achieve a significant induction of the callus in 223.3%.

TABLE 1

| ½ MS medium Formula | |
|---|---|
| Macroelements (mg/l) | |
| KNO₃ | 950 |
| NH₄NO₃ | 825 |
| CaCl₂•2H₂O | 220 |

TABLE 1-continued

| ½ MS medium Formula | |
|---|---|
| MgSO₄•7H₂O | 185 |
| KH₂PO₄ | 85 |
| Microelements (mg/l) | |
| Na₂EDTA | 37.3 |
| FeSO₄•7H₂O | 27.8 |
| KI | 0.38 |
| H₃BO₃ | 6.2 |
| MnSO₄•4H₂O | 22.3 |
| ZnSO₄•7H₂O | 8.6 |
| NaMoO₄•2H₂O | 0.25 |
| CuSO₄•5H₂O | 0.025 |
| CoCl₂•6H₂O | 0.025 |
| Organic compounds (mg/l) | |
| Thiamine-HCl | 1.0 |
| Nicotinic acid | 0.5 |
| Pyridoxine-HCl | 0.5 |
| Glycine | 2.0 |
| Myo-inositol | 100.0 |
| Others (g/l) | |
| Sucrose | 20 | pH 5.7

The chopped prothallium will generate the callus of 0.1 cm to 0.2 cm in diameter in 60 days. The chopped prothallium will still be cultured in the same medium under the same condition for another 80 to 100 days (preferably for 90 days) wherein it is sub-cultured every fifteen days during the culturing. This enables the callus to be quickly proliferated and massed in a round, forming a callus round in approximately 90 days. The callus round is 0.11 kg to 0.17 kg in weight, 0.19 cm to 0.25 cm in diameter and has a granular and rough surface. Generally, the callus round is green on the surface because it can continuously contact with the medium, but will be brown inside.

Finally, the callus round is further cultured in a culture fluid at 23° C. to 25° C. and 11 to 14 $\mu mol^{-2}\ s^{-1}$ (Light: Dark=16:8) for between to 150 days (preferably for 120 days), and are preferably sub-cultured every fifteen days till the callus round regenerates a sporophyte. In this situation, the callus round will keep on growing, and can reach 0.57 cm to 0.7 cm in diameter after approximately 60 days, and reach 1.2 cm to 1.34 cm in 120 days. In the present example, the culture fluid comprises ½ MS medium. In other examples, the culture fluid can further comprise 1 to 5 mg/l N6-(delta 2-isopentenyl)-adenine (2ip), 6-benzylaminopurine (BA) and kinetin, particularly for 1 mg/l N6-(delta 2-isopentenyl)-adenine (2ip). Under such condition, the proliferation of the callus round, as well as the regeneration of sporophytes, are all dramatically improved, with a proliferation rate of the callus reaching to 537±161.2% and an induction rate of sporophytes reaching 100% in 120 days. Additionally, a regenerated sporophyte of the present example can be further transplanted to a solid medium till it has more than 3 cm length (preferably for 3.5 cm length) for growing into a plant, wherein the plant has a survival rate of up to 90.3%.

Although the aforementioned example is preferably used on a fern of the Davalliaceae family, the tissue culturing method can also be used to culture other ferns which have calluses, such as *Osmunda cinnamomea* of the Osmundaceae family, *Ampelopteris prolifera* of the Thelypteridaceae family, *Asplenium nidus* of the Aspleniaceae family, *Adiantum raddianum* of the Adiantaceae family, *Dryopteris affinis* of the Dryopteridaceae family, *Platyceriaceae bifur-*

*catum* of the Platyceriaceae family, and *Drynaria quercifolia* of the Drynariaceae family. Some ferns which have a high economic value can be mass produced, as well as widely applied in industries, through the tissue culturing method of the present invention.

In the following, two experiments are performed to demonstrate how conditions of different media directly relate to the induction of calluses and sporophytes, with various media and liquid media comprising different conditions which are prepared and tested in the experiments.

Experiment 1:

In the present experiment, a plurality of 50 ml flasks are prepared, each having 0.1 g chopped prothallium of *Davallia mariesii* (in 0.1 cm to 0.2 cm pieces) being cultured in a medium therein, wherein the medium comprises 10 ml ½ MS medium (including a small amount of sucrose, namely 20 g/l sucrose) and various growth regulators in various amounts as listed in TABLE 2. After 60 days of culturing, calluses obtained in each flask are collected and analyzed respectively, to record the size, weight and number of each callus.

TABLE 2

Calluses Induction under Various Growth Regulators

| Growth Regulators (mg/L) | | Proliferation Rate | Calluses | |
|---|---|---|---|---|
| NAA | Kinetin | (%)[1] | (numbers)[2] | Appearances |
| 0 | 0 | 243.3 ± 33.0 | 95.33 ± 12.66 | green |
| 0 | 1 | 153.3 ± 24.9 | 73.67 ± 14.38 | green |
| 0 | 2 | 66.6 ± 17.0 | 21.00 ± 3.74 | green |
| 0 | 5 | 23.3 ± 4.7 | 6.00 ± 5.35 | green |
| 1 | 0 | 96.6 ± 17.0 | 54.33 ± 9.46 | brown |
| 1 | 1 | 223.3 ± 33.0 | 82.33 ± 4.99 | brown |
| 1 | 2 | 116.6 ± 53.1 | 47.00 ± 5.10 | green |
| 1 | 5 | 103.3 ± 17.0 | 31.67 ± 3.09 | green |
| 2 | 0 | 53.3 ± 20.6 | 23.67 ± 1.25 | brown |
| 2 | 1 | 43.3 ± 12.5 | 14.67 ± 5.44 | brown |
| 2 | 2 | 26.6 ± 4.7 | 4.67 ± 3.40 | brown |
| 2 | 5 | 26.6 ± 4.7 | 5.33 ± 3.77 | brown |
| 5 | 0 | 23.3 ± 4.7 | 0.00 ± 0.00 | — |
| 5 | 1 | 16.6 ± 4.7 | 0.00 ± 0.00 | — |
| 5 | 2 | 16.6 ± 4.7 | 0.00 ± 0.00 | — |
| 5 | 5 | 13.3 ± 4.7 | 0.00 ± 0.00 | — |

[1]Proliferation rate = (cell weight in each flask − 0.1 g) ÷ 0.1 g × 100%
[2]Numbers of callus round in 0.1-0.2 cm With reference to TABLE 2, it is shown that the medium of the present invention can effectively induce chopped gametophytes to generate calluses, especially when the medium only comprises basic salts, organic compounds and carbon source or is further accompanied with 1 mg/l NAA and 1 mg/l kinetin. It is noted that the calluses of different colors (green and brown) do not show great differences in callus proliferation.

Experiment 2:

In the present experiment, callus rounds, being 0.14±0.03 g and 0.21±0.02, are prepared wherein every four are cultured in a culture fluid to induce the callus rounds to regenerate sporophytes, wherein the medium comprises ½ MS medium (including a small amount of sucrose, namely 20 g/l sucrose) and various cytokinins in various amounts as listed in TABLE 3. After 60 days and 120 days of culturing, respectively, sporophytes obtained in each medium are collected and analyzed to record the size of the callus rounds and the number and length of sporophytes regenerated from the callus rounds.

TABLE 3

Sporophyte Regeneration under Various Cytokinins

| | 60 days | | | 120 days | | |
|---|---|---|---|---|---|---|
| Cytokinins | Proliferation Rate (%)[1] | Diameter (cm)[2] | Induction Rate (%)[3] | Proliferation Rate (%)[1] | Diameter (cm)[2] | Induction Rate (%)[3] |
| Control | 291.7 ± 49.4 | 0.71 ± 0.06 | 20.8 | 756.5 ± 241.4 | 1.20 ± 0.34 | 29.2 |
| 1 mg/L 2ip | 208.9 ± 24.1 | 0.57 ± 0.04 | 100.0 | 537.5 ± 161.2 | 1.34 ± 0.22 | 100.0 |
| 2 mg/L 2 ip | 156.0 ± 22.2 | 0.60 ± 0.03 | 100.0 | 386.3 ± 99.7 | 1.46 ± 0.21 | 100.0 |
| 5 mg/L 2ip | 64.9 ± 18.3 | 0.38 ± 0.03 | 0.0 | 208.3 ± 67.9 | 0.91 ± 0.24 | 8.3 |
| 1 mg/L BA | 40.5 ± 16.6 | 0.29 ± 0.05 | 0.0 | 191.1 ± 71.5 | 0.97 ± 0.15 | 0.0 |
| 2 mg/L BA | 89.9 ± 22.9 | 0.42 ± 0.06 | 0.0 | 300.0 ± 38.6 | 0.77 ± 0.13 | 0.0 |
| 5 mg/L BA | 41.1 ± 16.3 | 0.41 ± 0.06 | 0.0 | 216.7 ± 38.7 | 0.88 ± 0.16 | 0.0 |
| 1 mg/L Kinetin | 82.1 ± 24.3 | 0.31 ± 0.06 | 0.0 | 231.0 ± 83.5 | 0.63 ± 0.09 | 16.7 |
| 2 mg/L Kinetin | 47.0 ± 12.2 | 0.23 ± 0.05 | 0.0 | 182.1 ± 88.4 | 1.02 ± 0.06 | 0.0 |
| 5 mg/L Kinetin | 72.6 ± 17.5 | 0.32 ± 0.07 | 0.0 | 217.9 ± 70.9 | 1.13 ± 0.10 | 0.0 |

[1]Proliferation rate (%) = (weight of each callus round − 0.14 g) ÷ 0.14 g × 100%
[2]Diameters defined as a total value of the callus round and the sporophyte thereon
[3]Induction Rate (%) = Number of the callus round having the sporophyte ÷ Number of callus rounds = 100%

With reference to TABLE 3, it is shown that the culture fluid of the present invention induces the calluses to regenerate sporophytes, especially when the culture fluid comprises basic salts, organic compounds and carbon source solely or further accompanied with 1 mg/l to 2 mg/l N6-(delta 2-isopentenyl)-adenine (2ip).

Through the aforementioned experiments, it can be demonstrated that the tissue culturing method of the present invention effectively induces vascular plants to generate and proliferate calluses, and then regenerate sporophytes from the calluses. Hence the present invention provides a mass production strategy for vascular plants.

The present tissue culturing method is mainly characterized by inducing a chopped gametophyte of vascular plants to generate and proliferate embryogenic calluses, then forming a callus round, and inducing the callus round to regenerate a sporophyte, so that the present invention can be used to culture various valuable vascular plants, such as ferns of the Davalliacae family. Also, since the proliferating of embryogenic calluses and regenerating of sporophytes of the present invention are carried out by using culturing media, media which can continuously contact the embryogenic calluses and sporophytes in particular, such as liquid media, is sufficient to simplify the tissue culturing system, and improve both the culturing efficiency and quality. Therefore, the tissue culturing method of the present invention can be used for commercializing vascular plants.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A tissue culturing method of Davalliaceae family ferns, comprising following steps:
providing a chopped gametophyte of Davalliaceae family ferns;
generating a callus, by shaking culturing the chopped gametophyte of Davalliaceae family ferns in a liquid medium which comprises ½ MS salts and 20 g/L sucrose, till the chopped gametophyte of Davalliaceae family ferns generates the callus; and
performing apogamic regeneration of a sporophyte, by shaking culturing the calluses in a culture fluid which comprises ½ MS salts, 20 g/L sucrose, and 1-2 mg/L N6-(delta 2-isopentenyl)-adenine (2ip), to develop the sporophyte from the callus.

2. The tissue culturing method of claim 1, wherein the step of generating the callus further comprises:
inducing the chopped gametophyte of Davalliaceae family ferns to generate the callus; and
proliferating the generated callus.

3. The tissue culturing method of claim 1, wherein the step of apogamic regeneration of the sporophyte further comprises:
sporophyte induction, by inducing the callus to form the sporophyte; and
sporophyte proliferation, by proliferating the formed sporophyte.

4. The tissue culturing method of claim 1, wherein the step of apogamic regeneration the sporophyte comprises:
culturing the callus in a first culture fluid which comprises ½ MS salts, 20 g/L sucrose, and 1-2 mg/L N6-(delta 2-isopentenyl)-adenine (2ip), to induce the generating of the sporophyte from the callus; and
culturing the generated sporophyte in a second culture fluid to induce the proliferation of the generated sporophyte, wherein the first culture fluid and the second culture fluid comprise different compositions.

5. The tissue culturing method of claim 4, wherein the second culture fluid comprises no cytokinin, or comprises cytokinin being selected from the group consisting of N6-(delta 2-isopentenyl)-adenine (2ip), 6-benzylaminopurine (BA) and kinetin.

6. The tissue culturing method of claim 1 further comprising:
acclimatizing of the sporophyte, by isolating the sporophyte from the culture fluid; and
transplanting the sporophyte.

7. The tissue culturing method of claim 1 further comprising transplanting the sporophyte in a solid medium till a plant is grown.

* * * * *